US012692656B2

(12) United States Patent
Andersson et al.

(10) Patent No.: US 12,692,656 B2
(45) Date of Patent: Jul. 28, 2026

(54) DETERMINATION OF A PROPERTY OF A FIBER SUSPENSION

(71) Applicant: BTG INSTRUMENTS AB, Säffle (SE)

(72) Inventors: Niclas Andersson, Karlstad (SE); Jonny Weng, Säffle (SE); Hans Pettersson, Grums (SE); Karl Erik Rudander, Säffle (SE)

(73) Assignee: BTG INSTRUMENTS AB, Säffle (SE)

( * ) Notice: Subject to any disclaimer, the term of this patent is extended or adjusted under 35 U.S.C. 154(b) by 270 days.

(21) Appl. No.: 18/253,117

(22) PCT Filed: Nov. 19, 2021

(86) PCT No.: PCT/SE2021/051155
§ 371 (c)(1),
(2) Date: May 16, 2023

(87) PCT Pub. No.: WO2022/108512
PCT Pub. Date: May 27, 2022

(65) Prior Publication Data
US 2024/0003086 A1    Jan. 4, 2024

(30) Foreign Application Priority Data
Nov. 20, 2020    (SE) .................................... 2051356-0

(51) Int. Cl.
G01N 1/38 (2006.01)
B01F 23/40 (2022.01)
(Continued)

(52) U.S. Cl.
CPC ........... D21G 9/0018 (2013.01); B01F 23/43 (2022.01); B01F 23/483 (2022.01); B01F 31/65 (2022.01);
(Continued)

(58) Field of Classification Search
CPC ........... G01N 35/1016; G01N 35/1095; G01N 2035/1035; G01N 2001/1006;
(Continued)

(56) References Cited

U.S. PATENT DOCUMENTS

| | | | |
|---|---|---|---|
| 4,794,806 A | 1/1989 | Nicoli et al. | |
| 6,007,235 A | 12/1999 | Freud | |

(Continued)

FOREIGN PATENT DOCUMENTS

| | | | | |
|---|---|---|---|---|
| EP | 1331480 | * | 7/2003 | |
| EP | 1331480 A1 | * | 7/2003 | ........... G01N 33/343 |

*Primary Examiner* — Robert R Raevis
(74) *Attorney, Agent, or Firm* — DUANE MORRIS LLP; Gregory M. Lefkowitz; Daniel J. Tarr

(57) ABSTRACT

A method for determining a property of a fiber suspension comprises obtaining a sample and diluting the sample by a first dilution, thereby providing a diluted sample, while retaining essentially all of the sample, and mixing the diluted sample, thereby providing a mixed, diluted sample. By removing part of the mixed, diluted sample and retaining an amount of the mixed, diluted sample, further diluting the mixed, diluted sample by adding dilution water to the retained amount of the mixed, diluted sample, thereby providing a further diluted sample, while retaining essentially all of the mixed, diluted sample, mixing the further diluted sample, thereby providing a mixed, further diluted sample, and repeating these steps until the concentration is suitable for measuring the property of the further diluted sample, this property can be measured with high accuracy. A device for determining a property to be determined of a suspension is also provided.

5 Claims, 3 Drawing Sheets

(51) Int. Cl.

| | |
|---|---|
| *B01F 23/43* | (2022.01) |
| *B01F 31/65* | (2022.01) |
| *D21G 9/00* | (2006.01) |
| *G01N 33/34* | (2006.01) |
| *B01F 101/23* | (2022.01) |
| *B01F 101/47* | (2022.01) |

(52) U.S. Cl.
CPC ............. *G01N 1/38* (2013.01); *G01N 33/343* (2013.01); *B01F 2101/23* (2022.01); *B01F 2101/47* (2022.01)

(58) Field of Classification Search
CPC ..... G01N 2001/1012; G01N 2001/382; G01N 1/38; G05D 7/0694; B01L 2200/143; B01L 2200/16; B01L 2300/0654; B01L 2400/0481; B01L 2400/0487; B01L 3/50273; G01F 1/7086
USPC ........... 73/53.03, 53.04, 61.71, 61.72, 64.44, 73/64.56, 864.22, 864.81, 866; 348/86; 348/88; 162/198
See application file for complete search history.

(56) References Cited

U.S. PATENT DOCUMENTS

| | | |
|---|---|---|
| 2003/0174306 A1 | 9/2003 | Grant et al. |
| 2008/0134805 A1 | 6/2008 | Blasco et al. |
| 2008/0250848 A1* | 10/2008 | Karki .................... D21H 23/78 73/54.01 |
| 2014/0250987 A1 | 9/2014 | Thomas et al. |
| 2019/0218715 A1* | 7/2019 | Antensteiner ............. D21F 7/00 |

\* cited by examiner

DETERMINATION OF A PROPERTY OF A FIBER SUSPENSION

CROSS-REFERENCE TO RELATED APPLICATIONS

This application is a § 371 national stage entry of International Application No. PCT/SE2021/051155, filed Nov. 19, 2021, which claims priority to Sweden Application No. 2051356-0, filed Nov. 20, 2020, the entire contents of which are incorporated herein by reference.

TECHNICAL FIELD

The present invention relates generally to a method and a device for determining a property of a fiber suspension, especially a pulp fiber suspension.

BACKGROUND ART

The process efficiency of a pulp mill or paper mill is a complex function, and it depends on for example the pulp type, the pulp properties, the process equipment, and the conditions used.

While not every single property and constituent can be measured in every process stage the inherent challenge is to identify the key process parameters, to measure and base process control solutions on those parameters, in order to achieve high quality and productivity. One such key process parameter is the morphological properties of the pulp suspension, including for example mean fiber length, fiber length distribution, and content of fines and shives.

In a pulp suspension, the concentration of fibers is relatively high. Thus, in order to determine for example the characteristics of individual fibers in the suspension, this must be diluted to a large degree before measuring and determination of the characteristics. In other words, determination of such characteristics is not possible in in-line measuring systems. Instead, a sample must be taken from the suspension in the process pipe for subsequent dilution and determination.

In such measuring systems where a sample is obtained in a process plant, for example in a pulp and paper process, samples are typically obtained in several locations and are forwarded to a stationary, large central unit, where the samples are diluted and then analyzed, one at a time. This sequential measuring process leads to delays and relatively low measuring frequency, which may be detrimental to the process control.

In a dilution process, there is always a risk that the properties of a diluted sample are not representative for the suspension from which the original sample was taken. This in turn may lead to inaccurate measurement results.

Measurement systems can be adapted for a continuous measuring process or a batchwise process. In a continuous measuring process, there is a continuous supply of the fiber suspension to the measurement system while in a batchwise measuring process, a first amount of fiber suspension is provided to the measurement system and this amount is treated and the property thereof is determined before another amount of fiber suspension is provided.

SUMMARY OF INVENTION

An object of the present invention is to provide a method and a device for determining a property to be determined of a fiber suspension, especially a pulp fiber suspension, which preferably is supplied batchwise to the device, which is faster, more efficient and accurate than prior art solutions.

The invention is based on the insight that by first mixing a diluted sample of a fiber suspension without losing any part thereof and then retaining part of this mixed, diluted sample, fractionation of the sample to be analyzed is avoided or at least minimized.

According to a first aspect of the invention, a method for determining a property to be determined of a fiber suspension, especially a pulp fiber suspension, is provided, the method comprising the following steps: a) obtaining a sample of the suspension, b) diluting the sample by a first dilution by adding dilution water to the sample, thereby providing a diluted sample, while retaining essentially all of the sample, c) mixing the diluted sample, thereby providing a mixed, diluted sample, and d) optionally, measuring the concentration of the mixed, diluted sample, the method being characterized by the following steps: e) removing part of the mixed, diluted sample and retaining an amount of the mixed, diluted sample, f) further diluting the mixed, diluted sample by adding dilution water to the retained amount of the mixed, diluted sample, thereby providing a further diluted sample, while retaining essentially all of the mixed, diluted sample, g) mixing the further diluted sample in a single mixing chamber, thereby providing a mixed, further diluted sample, h) optionally, measuring the concentration of the mixed, further diluted sample, repeating steps e)—h) until the concentration of the mixed, further diluted sample is suitable for measuring the property to be determined of the further diluted sample, and measuring the property to be determined of the further diluted sample.

By providing a system in which the dilution process is quick and efficient and in which the diluted sample is representative for the suspension from which the original sample was taken, several dilutions can be made in a short time. This in turn sets lower demands on the size of the dilution chamber since every dilution can be made to a relatively low ratio. Since the dilution chamber represents a large portion of the overall size of the device, a smaller dilution chamber results in a relatively small device which is advantageous for mounting to a process pipe. This also keeps costs down, which makes it feasible to replace a single, large, central unit with a plurality of devices, each mounted to or in the vicinity to a respective process pipe.

In a preferred embodiment, the property to be determined is any of the following: fiber length distribution, mean fiber length, content of fines and content of shives.

In a preferred embodiment, in step e), the amount of the mixed, diluted sample is retained in a mixing chamber.

In a preferred embodiment, the step g) of mixing comprises imparting a reciprocating movement of a plunger.

In a preferred embodiment, the first step of diluting the samples comprises diluting the sample at a ratio of less than 100:1, preferably a ratio of less than 50:1, and even more preferably a ratio of less than 20:1.

In a preferred embodiment, each step of further diluting the samples comprises diluting the sample at a ratio of less than 10:1, preferably a ratio of less than 5:1, and even more preferably a ratio of less than 3:1.

In a preferred embodiment, the sample of a fiber suspension is obtained batchwise.

According to a second aspect of the invention, a device for determining a property to be determined of a fiber suspension, especially a pulp fiber suspension, is provided, the device comprising: a dilution chamber connectable to a process pipe for obtaining a sample of a fiber suspension from the process pipe, the dilution chamber comprising a dilution inlet for dilution water, and an outlet for removing diluted sample from the dilution chamber, the device being characterized by a single mixing chamber different from the dilution chamber and comprising means for mixing fluid in the mixing chamber, the mixing chamber being connected to the dilution chamber. By providing different chambers for dilution and mixing, part of the mixed fluid can be retained in the mixing chamber during the dilution process to ensure that a representative amount of the diluted fluid is retained for the subsequent dilution step.

In a preferred embodiment, a measuring cell is provided interconnecting the dilution chamber and the mixing chamber.

In a preferred embodiment, the means for mixing fluid in the mixing chamber is a plunger adapted for reciprocal movement. Alternatively, the means for mixing fluid in the mixing chamber is a pump at a first side the pump is in fluid connection with the measuring cell and at a second side opposite the first side is in direct fluid connection with the dilution chamber.

In a preferred embodiment, the dilution chamber has a volume of less than 4 liters, preferably less than 2 liters, and even more preferably less than 1 liter.

In a preferred embodiment, the mixing chamber has a volume of between 0.05 and 1.0 liters, preferably between 0.1 and 0.5 liters, and even more preferably between 0.2 and 0.3 liters.

In a preferred embodiment, a gate is provided in fluid connection with the dilution chamber and is adapted to be attached to a process pipe. The gate preferably comprises a valve adapted to be controlled to regulate the amount of fiber suspension of the sample to be analyzed.4. In this way, fluid suspension can be supplied batchwise to the device.

BRIEF DESCRIPTION OF DRAWINGS

The invention is now described, by way of example, with reference to the accompanying drawings, in which.

DESCRIPTION OF EMBODIMENTS

Figures 1, 4:
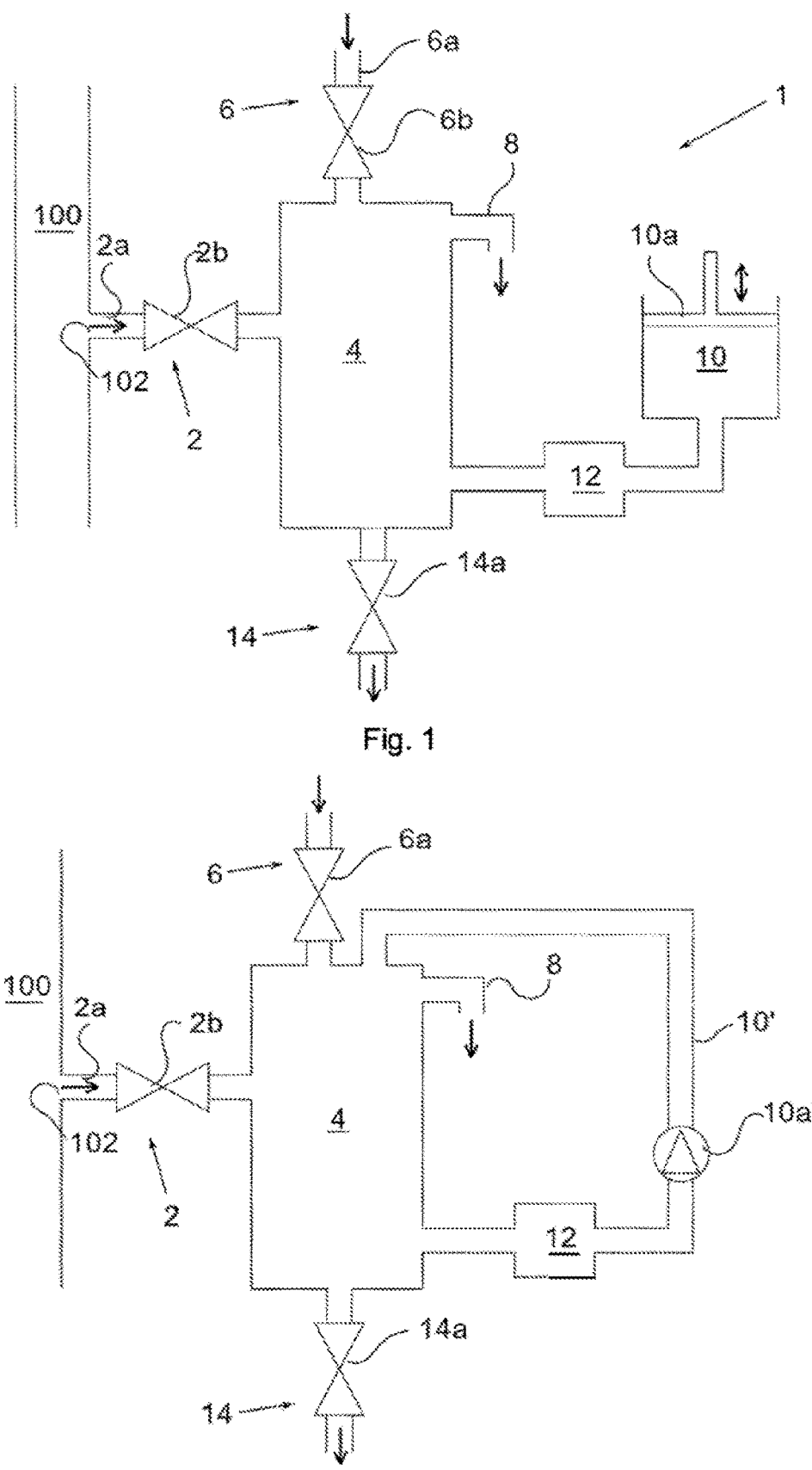
FIG. 1 is an overall diagram of a device for determining a property of a fiber suspension according to the invention.

In the following, a detailed description of a method and a device for determining a property of a fiber suspension, especially a pulp fiber suspension, will be given with reference mainly to FIG. 1.

The device for determining a property of a suspension is generally designated 1. The device 1 comprises a gate 2 which is adapted to be attached to an opening 102 of a process pipe 100. The process pipe may be a pulp process pipeline conveying a fiber suspension of a paper mill, for example. The gate 2 is shown schematically in FIG. 1 and comprises an attachment portion 2*a* adapted to be attached to the process pipe by means of for example bolts, covering an opening 102 in the process pipe 100. The gate 2 also comprises a valve or sluice 2*b* controlled to regulate the amount of fiber suspension, i.e., the volume, of the sample to be analyzed. This means that the valve 2*b* can be controlled in such way that the fiber suspension is supplied batchwise to the device. In a preferred embodiment, a sample of for example 25 ml is obtained from the process pipe 100, whereby a sample with a sufficient number of fibers, i.e., tens or hundreds of thousands of fibers, is obtained. It will be appreciated that the volume of the sample obtained from the process pipe 100 may vary widely, depending on the design of the device etc.

The sample obtained from the process pipe 100 is forwarded to a dilution chamber 4, in which the sample is diluted by a pre-dilution by adding dilution water to the sample, thereby providing a pre-diluted sample. To this end, a dilution inlet, generally designated 6, is provided in the dilution chamber 4. Although the dilution inlet 6 is shown to be in the upper portion of the dilution chamber 4, it is appreciated that it can be provided in other portions, such as in a side wall of the dilution chamber 4. The dilution inlet 6 comprises a pipe 6*a* connected to a source of water for dilution and a valve 6*b* controlled to regulate the amount of dilution water added to the sample.

A dilution overflow outlet 8 is also provided in the upper portion of the dilution chamber 4. The function of the overflow outlet 8 is to allow excess diluted sample to exit the dilution chamber in case it is filled. In addition to the overflow outlet 8, there is provided an outlet in the form of a drain 14 with a drain valve 14*a* in the bottom of the dilution chamber 4. By means of the drain valve 14*a*, controlled emptying of the dilution chamber 4 can be achieved.

Depending on pulp type and the pulp concentration in the process pipe, it is preferred that the pre-dilution of the sample is performed at a ratio of less than 100:1, preferably a ratio of less than 50:1, and even more preferably a ratio of less than 20:1

During this first pre-dilution process, it is important that essentially all of the sample is retained. For example, it is important that only a negligible portion of the sample leaves through the overflow outlet 8. In other words, a representative aliquot, i.e., mixed, pre-diluted sample must be obtained. In a preferred embodiment, in this pre-dilution process, the sample is diluted by a factor of about 20, although this may vary widely, depending on the circumstances. For example, the volume of the dilution chamber 4 is limited, which means that the degree to which a sample can be diluted in a single step is limited. In a preferred embodiment, the dilution chamber 4 has a volume of less than 4 liters, preferably less than 2 liters, and even more preferably less than 1 liter.

As an alternative to adding dilution water to a sample in the dilution chamber 4, a sample can be taken into the dilution chamber 4 which has been pre-filled with water and then optionally fill with additional dilution water until the fibers start to leave the dilution chamber through the outlet 8.

Figure 2A:
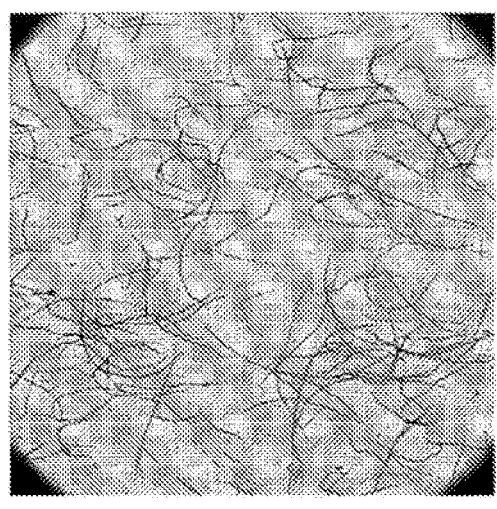
FIG. 2*a* is a picture showing fibers in a fiber suspension with a relatively high concentration, such as directly after pre-dilution.

After the sample has been pre-diluted, it is mixed, thereby providing a mixed, diluted sample. The mixing ensures that the fibers in the diluted sample is essentially evenly distributed throughout the mixed, diluted sample. An example of a pre-diluted sample is shown in FIG. 2*a*. By means of the dilution process, the concentration is relatively lower in the mixed, diluted sample as compared to the sample obtained from the process pipe 100.

To achieve mixing, a mixing chamber 10 is provided. The mixing chamber 10 is connected to the dilution chamber 4 via a measuring cell 12. This means that the dilution chamber 4 and the mixing chamber 10 are different chambers. The mixing is achieved by means of a mixing device in the form of a plunger 10a adapted for reciprocating movement between a lower end position and an upper end position, as seen in FIG. 1. By means of the plunger, the volume of the mixing chamber 10 can be adjusted, whereby part of the diluted sample in the dilution chamber is brought into the mixing chamber 10 when the volume thereof increases, i.e., when the plunger 10a moves upward. During this phase, the sample passes the measuring cell 12 and the concentration of the mixed, diluted sample, may optionally be measured. When the plunger 10a moves downward towards its lower end position, the mixed, diluted sample is forced the other way, i.e., back into the dilution chamber 4. After a number of strokes of the plunger 10a, preferably about 3 strokes, the diluted suspension has been sufficiently mixed. In a preferred embodiment, the mixing chamber 10 has a volume of between 0.05 and 1.0 liters, preferably between 0.1 and 0.5 liters, and even more preferably between 0.2 and 0.3 liters After this initial pre-dilution and mixing process, part of the mixed, diluted sample is removed and an amount of the mixed, diluted sample, is retained in the mixing chamber 10. To achieve this removal, the drain valve 14a is opened, allowing the mixed, pre-diluted sample in the dilution chamber 4 to leave. Alternatively or additionally, the dilution chamber 4 may be flushed with water from the dilution inlet 6 until essentially all of the diluted sample in the dilution chamber 4 has been flushed out through the overflow outlet 8. During this process, the part of the mixed, pre-diluted sample which is in the mixing chamber 10 and possibly also in the connecting pipe and the measuring cell 12 is retained there by the vacuum effect. Optionally, a valve (not shown) in the pipe interconnecting the dilution chamber 4 and the mixing chamber 10 may be provided to ensure that an amount of the mixed, diluted sample, is retained in the mixing chamber 10. It will be realized that the volume of the dilution chamber 4 must be larger than the volume of the mixing chamber 10. Otherwise, all of the mixed, diluted sample would be in the mixing chamber and adjoining parts, such as the measuring cell 12 and connecting pipes, and no part thereof would be removed through the drain 14. It will also be appreciated that the volume of the mixing chamber may be adjusted by means of the plunger 10a between a minimum volume when the plunger is in its lower end position as seen in FIG. 1 and a maximum volume when the plunger is in its upper end position as seen in FIG. 1.

It is important that the dilution process takes place essentially without fractionation, i.e., that the diluted suspension is divided into non-representative parts and that a non-representative part of the suspension is removed. With the above-described process, wherein the pre-diluted sample is thoroughly mixed before part of it is removed and an aliquot is retained, fractionation is essentially prevented.

The mixed, pre-diluted sample is further diluted by adding dilution water from the dilution inlet 6 to the dilution chamber 4. The diluted sample retained in the mixing chamber 10 is then mixed with the dilution water by means of the mixing device, i.e., the plunger 10a, as described above, thereby providing a mixed, further diluted sample. In order to keep track of the concentration of the mixed, further diluted sample, this can optionally be measured in the measuring cell 12.

These steps, i.e., removing part of mixed, diluted sample and retaining an amount of the mixed, diluted sample, further diluting the mixed, diluted sample retaining essentially all of the mixed, diluted sample, and mixing the further diluted sample are repeated until the concentration of the mixed, further diluted sample is suitable for measuring the property to be determined of the further diluted sample. This concentration is usually between 1000 and 10000 lower than the concentration of the original sample obtained from the process pipe 100, but it may be lower or higher, depending on the circumstances. In each of these the steps of further diluting the samples, the sample is preferably diluted at a ratio of less than 10:1, preferably a ratio of less than 5:1, and even more preferably a ratio of less than 3:1.

Figure 2B:
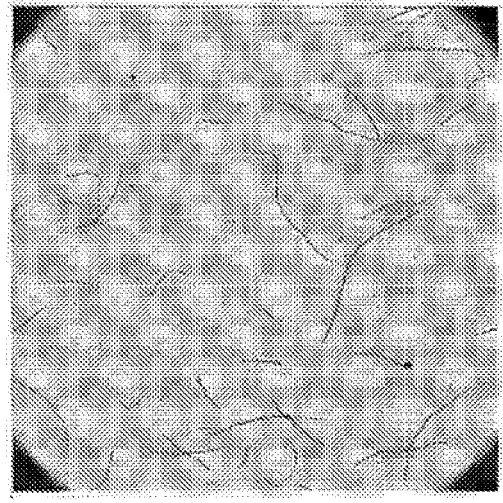
FIG. 2*b* is a picture showing fibers in a fiber suspension with a relatively low concentration after dilution.
Figure 2C:
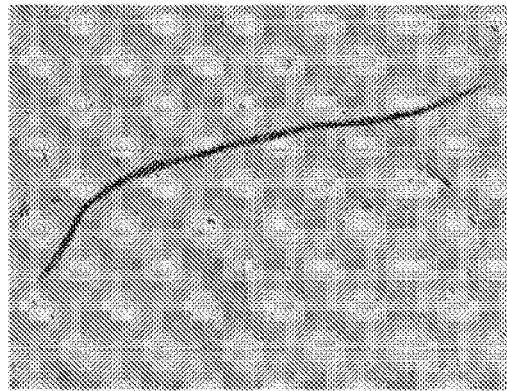
FIG. 2*c* is an enlarged picture showing a single fiber of a fiber suspension.
Figure 3:
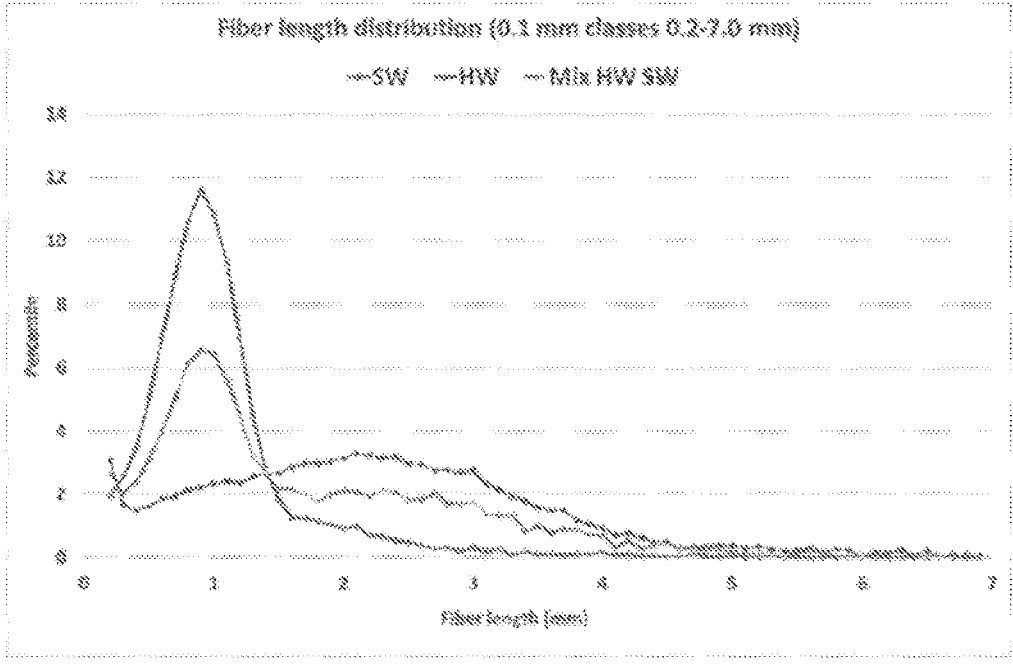
FIG. 3 is a diagram showing an example of fiber length distribution, and FIG. 4 an overall diagram of an alternative embodiment of a device for determining a property of a fiber suspension according to the invention.

In a final step, the property to be determined of the further diluted sample is measured by means of the measuring cell. The measuring cell 12 is adapted to measure properties of the sample as well as optionally the concentration thereof. The measuring cell preferably comprises a camera by which pictures of the sample can be acquired, as in the examples of FIGS. 2a-2c, where it is seen that the sample contains fibers of different lengths, widths and surface structures. The dilution facilitates analyzing of the properties of the suspension in the process pipe 100 and an enlarged picture of a single fiber is shown in FIG. 2c. Thus, the properties to be measured may include, but are not limited to, the composition of fiber length distribution, mean fiber length, and content of fines and shives. An example of a diagram showing the fiber length distribution is given in FIG. 3.

A device according to the invention for determining a property to be determined of a suspension thus comprises a dilution chamber 4 connectable to a process pipe 100 for obtaining a sample of a suspension from the process pipe. Preferably, a gate 2 with an attachment portion 2a and a valve 2b facilitates the sampling of samples with a predetermined volume from the process pipe 100.

The dilution chamber 4 comprises a dilution inlet 6 for dilution water, and an overflow outlet 8 for removing diluted sample from the dilution chamber. A drain 14 with a drain valve 14a is provided in the lower portion of the dilution chamber 4 for the removal of diluted sample from the dilution chamber 4.

A mixing chamber 10 comprises means 10a for mixing fluid in the mixing chamber 10, preferably a plunger adapted for reciprocating movement, wherein the mixing chamber 10 is connected, either directly or indirectly via a measuring cell 12 and/or a valve, to the dilution chamber 4 If no measuring cell is provided in the pipe interconnecting the dilution chamber 4 and the mixing chamber 10, it may be provided for example in the mixing chamber itself.

In an alternative embodiment of a device according to the invention for determining a property to be determined of a suspension, shown in FIG. 4, the mixing chamber and the plunger have been replaced by a mixing pipe 10' which at a first end connects to the measuring cell 12, as in the first embodiment, and in a second end opposite the first end connects to the upper portion of the dilution chamber 4. A pump 10a' replaces the plunger 10a and functions to circulate the diluted sample in the dilution chamber 4 to achieve mixing thereof. In this embodiment, the volume of the mixing pipe 10' corresponds to that of the mixing chamber 10 in the first embodiment. Thus, during the dilution process, an amount of the mixed, diluted sample is retained in the mixing pipe 10' while the dilution chamber 4 is emptied by means of the drain 14.

Preferred embodiments of a method and a device according to the invention for determining a property of a fiber suspension have been described. It will be realized that these may be modified within the scope of the appended claims. For example, the term mixing device is any device that accomplished mixing, such as a stirrer.

The invention claimed is:

1. A method for determining a property of a fiber suspension, the method comprising the following steps:

a) obtaining a sample of the fiber suspension, b) diluting the sample by a first dilution by adding dilution water to the sample, thereby providing a diluted sample, while retaining all of the sample obtained in step a), c) mixing the diluted sample using a single mixing chamber, thereby providing a mixed, diluted sample, and d) removing part of the mixed, diluted sample and retaining an amount of the mixed, diluted sample provided in step c), e) further diluting the mixed, diluted sample by adding dilution water to the retained amount of the mixed, diluted sample retained in step d), thereby providing a further diluted sample, while retaining all of the retained amount of the mixed, diluted sample retained in step d), f) mixing the further diluted sample provided in step e) using the single mixing chamber, thereby providing a mixed, further diluted sample, g) repeating steps d)-f) until the concentration of the mixed, further diluted sample is suitable for measuring the property to be determined of the further diluted sample, and h) measuring the property to be determined of the further diluted sample.

2. The method according to claim 1, wherein the property of the fiber is any of the following: fiber length distribution, mean fiber length, content of fines and content of shives.

3. The method according to claim 1, wherein, in step d), the amount of the mixed, diluted sample is retained in the single mixing chamber.

4. The method according to claim 1, wherein the step f) of mixing comprises imparting a reciprocating movement of a plunger.

5. The method according to claim 1, wherein in step a) a sample of a fiber suspension is obtained batchwise.

\* \* \* \* \*